United States Patent [19]

Nelson

[11] Patent Number: 5,015,632

[45] Date of Patent: May 14, 1991

[54] CHITOSAN PYRITHIONE AS AN ANTIMICROBIAL AGENT USEFUL IN PERSONAL CARE PRODUCTS

[75] Inventor: John D. Nelson, Naugatuck, Conn.

[73] Assignee: Olin Corporation, Cheshire, Conn.

[21] Appl. No.: 562,507

[22] Filed: Aug. 2, 1990

Related U.S. Application Data

[63] Continuation-in-part of Ser. No. 461,720, Jan. 8, 1990, Pat. No. 4,957,908.

[51] Int. Cl.$^5$ .................. A61K 31/00; C08B 37/00
[52] U.S. Cl. ........................ 514/55; 536/20; 536/55.2
[58] Field of Search .............. 536/20, 55.2; 514/55, 514/844, 846, 847; 546/290, 292, 298, 6; 604/358, 360, 364

[56] References Cited

U.S. PATENT DOCUMENTS

| | | | |
|---|---|---|---|
| 3,879,376 | 4/1975 | Valerberghe et al. | 536/20 |
| 3,953,608 | 4/1976 | Vanlerberghe et al. | 536/20 |
| 4,048,181 | 9/1977 | Douglass | 546/292 |
| 4,122,084 | 10/1978 | Douglass | 546/6 |
| 4,122,085 | 10/1978 | Douglass | 546/292 |
| 4,345,080 | 8/1982 | Bolich | 546/6 |
| 4,528,283 | 7/1985 | Lang et al. | 536/20 |
| 4,533,736 | 8/1985 | Trotz et al. | 546/290 |
| 4,632,991 | 12/1986 | Maurer et al. | 546/6 |
| 4,659,700 | 4/1987 | Jackson | 514/55 |
| 4,659,830 | 4/1987 | Maurer et al. | 546/6 |
| 4,670,430 | 6/1987 | Imamura et al. | 546/6 |
| 4,845,204 | 7/1989 | Lang et al. | 536/20 |
| 4,957,908 | 9/1990 | Nelson | 514/55 |

*Primary Examiner*—Ronald W. Griffin
*Assistant Examiner*—Everett White
*Attorney, Agent, or Firm*—Dale Lynn Carlson

[57] ABSTRACT

In accordance with the present invention, a new pyrithione salt, namely chitosan pyrithione, is produced. This composition is characterized by a combination of slow release from films and excellent antimicrobial activity. The antimicrobial activity is equivalent to that of sodium pyrithione. These properties make chitosan pyrithione potentially useful as an antimicrobial agent in a variety of dermatological items, such as soaps, shampoos, and skin care medicaments.

4 Claims, No Drawings

CHITOSAN PYRITHIONE AS AN ANTIMICROBIAL AGENT USEFUL IN PERSONAL CARE PRODUCTS

BACKGROUND OF THE INVENTION

This application is a continuation-in-part of U.S. application Ser. No. 07/461,720, filed Jan. 8, 1990, now U.S. Pat. No. 4,957,908.

Chitosan is the deacetylated derivative of the polysaccharide chitin [B-(1-4)-poly-N-acetyl-D-glucosamine], an abundant natural by-product of the crab and shrimp industries. Chitosan is known to be fungicidal for both animal and plant pathogens provided this substance is not a component of the fungal cell wall. Films of chitosan salts have proven useful in healing wounds.

Pyrithione salts, such as zinc and sodium pyrithione which are commercially available under Olin Corporation's registered trademark OMADINE ®, are known to have broad antibacterial and antifungal activity. However, because these pyrithione salts are absorbed through the skin fairly rapidly, they may only be used at relatively low concentrations in products intended for topical application. Accordingly, new forms of pyrithione that are more slowly absorbed into the skin would be of significant interest to the skin care industry.

SUMMARY OF THE INVENTION

In accordance with the present invention, a new pyrithione salt, namely chitosan pyrithione, is provided having the following empirical structural formula:

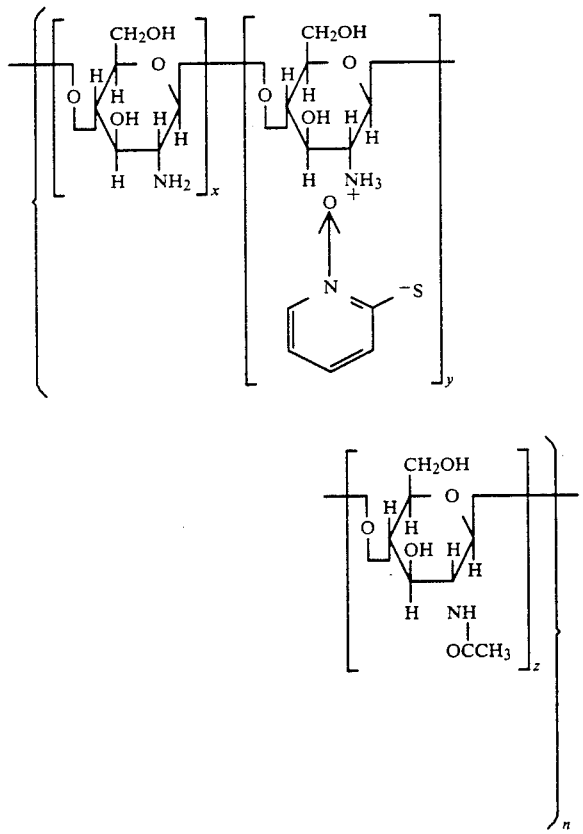

wherein x, y and z are independently molar fractions having values between 0.01 and 0.98 with the proviso that $x+y+z=1$, and n has a value between about 700 and about 10,000 (preferably between about 700 and about 3,000). Preferably y has a value between about 0.3 and about 0.7, more preferably between about 0.4 and about 0.6.

This compound is an excellent film former which is characterized by a combination of a slow release of pyrithione and excellent antimicrobial activity. The antimicrobial activity is equivalent to sodium pyrithione. These properties make chitosan pyrithione potentially useful as an antimicrobial agent in a variety of dermatological items, such as soaps, and skin care medicaments.

DETAILED DESCRIPTION OF THE INVENTION

In accordance with the present invention, chitosan pyrithione can be prepared either by reacting a chitosan salt, such as chitosan acetate, with a pyrithione salt, such as sodium pyrithione, or by neutralization of chitosan, which is a weak base, with a pyrithione acid. The antimicrobial activity of each of these preparations is illustrated in the examples given below. These and other aspects will become apparent upon reading the following detailed description of the invention.

The molecular weight of commercially available chitosan is typically between about 100,000 and about 2,000,000. Using this reactant, chitosan pyrithione is produced by the addition of pyrithione as described above. The average molecular weight of the resulting chitosan pyrithione polymer is typically in the range of between about 150,000 and over two million, more typically in the range of between about 150,000 and about 600,000.

The chitosan pyrithione product has many desirable attributes. Pyrithione possesses good antimicrobial activity, and is compatible with components of conventional soaps, shampoos, skin-care medicaments, and the like. It is also non-volatile, hydrolytically-stable, thermally-stable, and soluble in water and common organic solvents. Furthermore, it forms no undesirable colors in typical personal care items. Chitosan is also used in cosmetic products.

The chitosan pyrithione is suitably employed in an antimicrobially-effective amount in a desired dermatological or other personal care product. This "antimicrobially-effective amount" is preferably between about 0.1 and 30 weight percent of such chitosan pyrithione based upon the total weight of the personal care product.

The following examples are intended to illustrate, but in no way limit, the scope of the present invention.

EXAMPLE 1

Preparation of Chitosan Pyrithione and Testing of Its Antimicrobial Activity Against Phytophthora Parasitica Chitosan Pyrithione was prepared by dissolving 1% chitosan (crab shell, Sigma) in 1% OMADINE acid (pyrithione). The solution was dialyzed extensively against distilled water to remove excess acid. Based on volume before and after dialysis, the final chitosan concentration was estimated to be 0.55%. The pyrithione concentration, determined by a spectrophotometric assay, was 0.29% or approximately 52.7% of the polymer. The pyrithione concentration was slightly higher than the 40.6% expected if the polymer were fully substituted. However, total weight was estimated in this experiment, and this may account for the disparity.

A control solution of chitosan acetate was prepared by dissolving chitosan in 1% acetic acid. After dialysis, the final chitosan acetate concentration was estimated to be 0.9%. Phytophthora zoospore suspensions were mixed with serial dilutions of the chitosan solutions, and after 1 hour contact, plated on corn meal agar. Spores were also examined microscopically for motility. Zoospores remained viable after treatment with 45 ppm chitosan acetate but were killed by 90 ppm. In contrast, exposure to only 2.75 ppm chitosan pyrithione killed the zoospores.

Another sample of chitosan pyrithione was prepared by neutralization of chitosan (Sigma Chemical's "practical grade") in OMADINE acid. The chitosan reactant was determined to be 89.3% deacetylated, as measured by UV spectrophotometry, and contained negligible amounts of sulfur. Pyrithione ion separated from the chitosan backbone in gel permeation chromatograms, indicating the non-covalent nature of its attachment. The weight average molecular weight and the number average molecular weight of the separated chitosan were 446,288 and 118,583, respectively, and the polydispersity index was 3.76, as measured against polyvinylpyridine standards.

Chemical analysis by HPLC and an agar diffusion bioassay with *Staphylococcus aureus* ATCC 6538 indicated that the material contained 20.5% and 22.1% by weight of pyrithione ion, respectively. The theoretical maximum content of pyrithione in the compound is 40%, and so the test sample is substituted to an extent of approximately 50% of the theoretical maximum. The elemental composition of the polymer, particularly the sulfur content, is consistent with this conclusion.

|  | Weight Percent | | | |
|---|---|---|---|---|
|  | C | H | N | S |
| Chitosan Pyrithione (theory-50% subst) | 46.1 | 6.1 | 9.3 | 6.6 |
| Chitosan Pyrithione (actual) | 43.1 | 6.4 | 8.5 | 6.7 |
| Chitosan (theory) | 45.0 | 6.8 | 8.5 | 0.0 |
| Chitosan (actual) | 40.3 | 6.7 | 7.5 | 0.65 |

The emperical structural formula of this polymer is as follows:

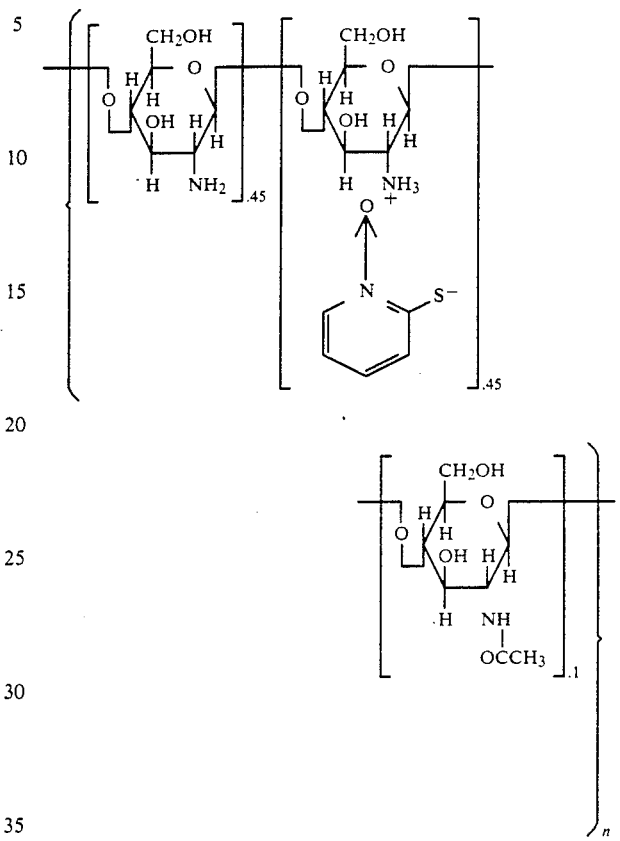

EXAMPLE 2

Determination of Minimum Inhibitory Concentrations (MICs) For Chitosan Pyrithione Against Varios Microorganisms Minimum inhibitory concentrations (MIC's) for the solutions prepared in Example 1 and for sodium Omadine were determined against 8 fungal and 8 bacterial strains as identified in Table 1 below.

The results as presented in Table 1 indicate that chitosan pyrithione demonstrated activity against all of the strains tested. In contrast, chitosan acetate was not effective against the strains tested.

TABLE 1

Activity of chitosan acetate, chitosan pyrithione, and sodium pyrithione against bacteria and fungi
MICs (in ppms of active moiety)

|  | Source | Chitosan Acetate | Chitosan Pyrithione | Sodium Pyrithione |
|---|---|---|---|---|
| Bacteria | | | | |
| *Pseudomanas aeruginosa* | cosmetic isolate | >1000 | 363 | 438 |
| *Pseudomonas aeruginosa* | shampoo isolate | >1000 | 725 | 875 |
| *Pseudomonas syringae* | ATCC 19310 | >1000 | 12 | 55 |
| *Pseudomonas syringae* | ATCC 11355 | >1000 | 2 | 3 |
| *Enterobacter aerogenes* | cosmetic isolate | >1000 | 12 | 109 |
| *Staphylococcus aureus* | ATCC 6538 | >1000 | 2 | 3 |
| *Xanthomonas campestris* | ATCC 11551 | >1000 | 22 | 27 |
| *Xanthomonas campestris* | ATCC 19315 | >1000 | <0.08 | <0.10 |
| Fungi | | | | |
| *Aspergillus niger* | ATCC 16404 | >2250 | 12 | 28 |
| *Penicillium levitum* | ATCC 10464 | >2250 | 0.4 | 0.1 |
| *Fusarium oxysporum* | ATCC 15643 | >2250 | 91 | 219 |
| *Helminthosporum oryzae* | ATCC 34393 | >2250 | <0.04 | <0.05 |

TABLE 1-continued

Activity of chitosan acetate, chitosan pyrithione, and sodium pyrithione against bacteria and fungi
MICs (in ppms of active moiety)

| | Source | Chitosan Acetate | Chitosan Pyrithione | Sodium Pyrithione |
|---|---|---|---|---|
| Glomerella cingulata | ATCC 10593 | >2250 | <0.04 | <0.05 |
| Alternaria solani | ATCC 11078 | >2250 | 0.4 | 0.5 |
| Rhizoctonia solani | ATCC 28268 | >2250 | <0.04 | <0.05 |
| Candida albicans | ATCC 10231 | >2250 | 2 | 0.5 |

EXAMPLE 3

Antifungal Activity of Chitosan Pyrithione and Chitosan Acetate Films

Chitosan pyrithione and chitosan acetate were prepared as in Example 1 and filter sterilized. Based on a dry weight of 1-2 ml. of material, the chitosan acetate concentration was 0.7%, and the chitosan pyrithione concentration was 0.96%. The pyrithione concentration constituted 21.5% of the chitosan pyrithione preparation, as determined by spectrophotometric assay.

Ten microliters of the solutions were spread on sterile 22 mm square glass coverslips and air-dried at room temperature to form a film. Coverslips were placed on Mycophil agar (BBL) plates and sprayed with a suspension of Aspergillus niger spores. Untreated coverslips were included as controls. Plates were incubated at 28° C. After 9 days, controls and chitosan acetate coated coverslips were overgrown by A. niger, and germinated spores were observed. The chitosan pyrithione film repelled fungal growth (see Table 2 below).

TABLE 2

Qualitative activity of chitosan films against Aspergillus niger

| Incubation Time (28° C.) | Control (no film) | Chitosan Acetate | Chitosan Pyrithione |
|---|---|---|---|
| 2 days | Confluent growth around coverslip, overgrowth and some germinated spores on coverslip | Same as control | Inhibition around coverslip; no growth on coverslip |
| 9 days | Germinated spores on coverslip | Germinated spores on coverslip | Confluent growth around coverslip; no germinated spores on coverslip. |

EXAMPLE 4

Preparation of Chitosan Pyrithione by Reacting Chitosan Acetate With Sodium Pyrithione To demonstrate that chitosan pyrithione can be prepared by a method other than by neutralization of pyrithione acid, sodium pyrithione was mixed with chitosan acetate and allowed to react for several hours before dialysis. After dialysis, the dry weight and pyrithione content of the chitosan pyrithione were determined. Based on dry weight, the solution contained 1.15% substituted polymer, and pyrithione comprised 8.95% of the polymer.

Antifungal activity was demonstrated using two samples of chitosan pyrithione, one prepared by acid neutralization following the procedure of Example 1 and the other by the reaction of salts as described in the preceding paragraph. The samples were spread on glass squares or coverslips and allowed to dry. The squares were placed on Mycophil agar (BBL) plates and overlaid with Mycophil agar inoculated with the fungus Candida albicans. Chitosan acetate films and untreated glass squares or coverslips were included as controls. Growth of the test organism was inhibited to a similar extent by both chitosan pyrithione preparations but not by the controls.

In the second type of experiment, 10 ul of each solution was pipetted onto 0.25 inch filter paper disks and allowed to dry. A control solution of aqueous sodium pyrithione was included. Treated disks were placed on Mycophil agar plates seeded with C. albicans. After incubation, zones of inhibition were measured. Both chitosan pyrithione solutions inhibited the test strain to the same degree as an equivalent amount of aqueous sodium pyrithione. In contrast, chitosan acetate showed no inhibitory effect.

What is claimed is:

1. Chitosan pyrithione having the empirical structural formula:

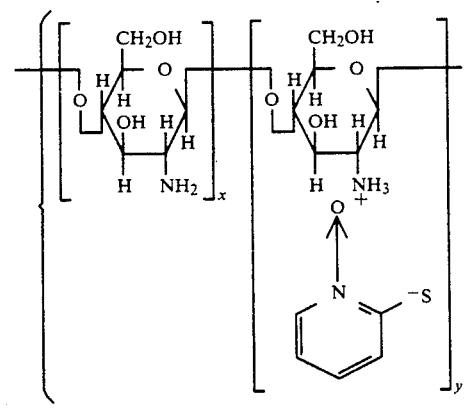

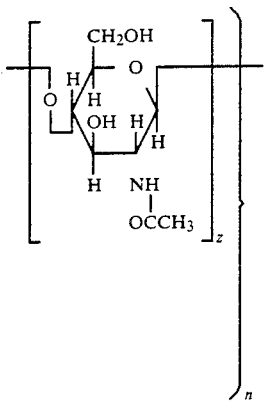

wherein x, y and z are independently molar fractions having values between 0.01 and 0.98 with the proviso that $x+y+z=1$, and n has a value between about 700 and about 10,000.

2. The chitosan pyrithione of claim 1 having an average molecular weight of between about 150,000 and about 600,000.

3. The chitosan pyrithione of claim 1 wherein y has a value of between about 0.3 and about 0.7.

4. The chitosan pyrithione of claim 3 wherein y has a value of between about 0.4 and about 0.6.

* * * * *